United States Patent
Sarachan et al.

(10) Patent No.: US 8,824,769 B2
(45) Date of Patent: *Sep. 2, 2014

(54) PROCESS AND SYSTEM FOR ANALYZING THE EXPRESSION OF BIOMARKERS IN A CELL

(71) Applicant: General Electric Company, Schenectady, NY (US)

(72) Inventors: Brion Daryl Sarachan, Schenectady, NY (US); Thomas Paul Repoff, Sprakers, NY (US); Colin Craig McCulloch, Ballston Lake, NY (US); Fiona Mary Ginty, Saratoga Springs, NY (US); Megan Pearl Rothney, Madison, WI (US); Zhengyu Pang, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/778,576

(22) Filed: Feb. 27, 2013

(65) Prior Publication Data

US 2013/0170728 A1 Jul. 4, 2013

Related U.S. Application Data

(63) Continuation-in-part of application No. 12/580,651, filed on Oct. 16, 2009, now abandoned.

(51) Int. Cl.
- *G06K 9/00* (2006.01)
- *G06F 19/18* (2011.01)
- *G06T 7/00* (2006.01)
- *G06F 19/24* (2011.01)

(52) U.S. Cl.
CPC ....... *G06F 19/18* (2013.01); *G06T 2207/20221* (2013.01); *G06F 19/24* (2013.01); *G06T 2207/30024* (2013.01); *G06T 2207/10056* (2013.01); *G06T 7/0081* (2013.01)
USPC .......................................................... 382/133

(58) Field of Classification Search
USPC .......................................................... 382/133
See application file for complete search history.

(56) References Cited

U.S. PATENT DOCUMENTS

| | | | |
|---|---|---|---|
| 6,569,624 B1 * | 5/2003 | Weindruch et al. | 435/6.13 |
| 6,999,607 B2 * | 2/2006 | Kiros et al. | 382/128 |
| 7,231,074 B2 | 6/2007 | Raunig | |
| 7,366,719 B2 * | 4/2008 | Shaw | 1/1 |

(Continued)

FOREIGN PATENT DOCUMENTS

| WO | WO2006110621 A2 | 10/2006 |
|---|---|---|
| WO | WO2007028161 A2 | 3/2007 |

(Continued)

OTHER PUBLICATIONS

Dolled-Filhart et al., "Classification of Breast Cancer Using Genetic Algorithms and Tissue Microarrays", Clin Cancer Res, vol. 12, No. 21, pp. 6459-6468, Nov. 1, 2006.

*Primary Examiner* — Michael Fuelling
(74) *Attorney, Agent, or Firm* — Eileen B. Gallagher

(57) ABSTRACT

The invention relates generally to a process of analyzing and visualizing the expression of biomarkers in an individual cell wherein the cell is examined to develop patterns of expression by using a grouping algorithm, and a system to perform and display the analysis.

5 Claims, 8 Drawing Sheets

(56) References Cited

U.S. PATENT DOCUMENTS

| | | |
|---|---|---|
| 7,711,174 B2 | 5/2010 | Sammak et al. |
| 7,713,695 B2 * | 5/2010 | Liew et al. .................. 435/6.18 |
| 8,320,655 B2 * | 11/2012 | Sarachan et al. ............. 382/133 |
| 2005/0048547 A1 | 3/2005 | Zhao et al. |
| 2006/0064248 A1 | 3/2006 | Saidi et al. |
| 2007/0092890 A1 * | 4/2007 | Abbas ............................. 435/6 |
| 2008/0032328 A1 * | 2/2008 | Cline et al. .................. 435/40.5 |
| 2008/0033657 A1 * | 2/2008 | Cline et al. ..................... 702/19 |
| 2008/0267471 A1 | 10/2008 | Yu et al. |
| 2008/0318800 A1 * | 12/2008 | Abbas ............................. 506/9 |
| 2009/0034823 A1 | 2/2009 | Christiansen et al. |
| 2009/0075395 A1 | 3/2009 | Lee et al. |
| 2009/0093969 A1 | 4/2009 | Ladd et al. |
| 2009/0204334 A1 * | 8/2009 | Semmes et al. ................. 702/19 |
| 2010/0106423 A1 | 4/2010 | Graf et al. |

FOREIGN PATENT DOCUMENTS

| | | |
|---|---|---|
| WO | WO2007130677 A2 | 11/2007 |
| WO | WO2008054768 A2 | 5/2008 |
| WO | WO2010020876 A2 | 2/2010 |

\* cited by examiner

PROCESS AND SYSTEM FOR ANALYZING THE EXPRESSION OF BIOMARKERS IN A CELL

CROSS-REFERENCE TO RELATED APPLICATIONS

This application is a continuation-in-part of pending U.S. patent application Ser. No. 12/580,651, filed Oct. 16, 2009.

BACKGROUND

The invention relates generally to a method of analyzing and visualizing the expression of biomarkers in individual cells wherein the cells are examined in situ in their tissue of origin to develop patterns of expression by numerical evaluation and a system to perform this analysis.

The examination of cells and tissues that have been treated to reveal the expression of biomarkers has long been a valuable tool for biological research and clinical studies. A common treatment has involved the use of antibodies or antibody surrogates such as antibody fragments that are specific for the biomarkers, commonly proteins, of interest. It is typical to directly or indirectly label such antibodies or antibody surrogates with a moiety capable, under appropriate conditions, of generating a signal. One approach has been to attach a fluorescent moiety to the antibody and to interrogate the treated tissue for fluorescence. The signal obtained is commonly indicative of not only the presence but also the amount of biomarker present.

The techniques of tissue treatment and examination have been refined so that the level of expression of a given biomarker in a particular cell or even a compartment of the given cell such as the nucleus, cytoplasm or membrane can be quantitatively determined Typically the boundaries of these compartments or the cell as a whole are located using well-known histological stains. Commonly the treated tissue is examined with digital imaging and the level of different signals emanating from different biomarkers can consequently be readily quantitated.

More recently a technique has been developed which allows testing a given tissue specimen for the expression of numerous biomarkers. Generally this technique involves staining the specimen with a fluorophore labeled probe to generate signal for one or more probe bound biomarkers, chemically bleaching these signals and re-staining the specimen to generate signals for some further biomarkers. The chemical bleaching step is convenient because there are only a limited number of signals that can be readily differentiated from each other so only a limited number of biomarkers can be examined in a particular step. But with bleaching, the sample may be re-probed and re-evaluated for multiple steps. This cycling method may be used on formalin fixed paraffin embedded tissue (FFPE) samples and cells. Digital images of the specimen are collected after each staining step. The successive images of such a specimen can conveniently be kept in registry using morphological features such as DAPI stained cell nuclei, the signal of which is not modified by the chemical bleaching method.

Another approach has been to examine frozen tissue specimens by staining them iteratively and photo bleaching the labels from the previous staining step before applying the next set of stains. The strength of the fluorescent signal associated with each biomarker evaluated is then extracted from the appropriate image.

There have been efforts to utilize this data to identify patterns of biomarker expression. One approach has been to look for such patterns in an entire tissue specimen and to binarize the fluorophore signals using threshold values and generate various expression profiles that are then overlaid on an image of the tissue of interest.

BRIEF DESCRIPTION

The invention relates generally to a process of analyzing and visualizing the expression of biomarkers in an individual cell wherein the cell is examined to develop patterns of expression by numerical evaluation and a system to perform this analysis.

In one embodiment a process is provided comprising measurement of the level of expression of multiple biomarkers in an individual cell. The measurement of biomarker expression within the cell is stored as a data point in a database and the database is interrogated for data points having a similar pattern of biomarker expression using a computer algorithm where such similarity is determined by a numerical analysis that uses the level of expression of each biomarker as at least a semi-continuous variable. The data points with minimum variance is identified and grouped together. The group is assigned a new biomarker expression profile represented by a new data point, which is based on a central value for each attribute considered by the algorithm, thus forming a new data set. The steps are repeated with the new data set until a predetermined number of groups are generated.

In another embodiment, a method for using the grouping data for displaying cellular components or groupings having similar patterns of expression of certain biomarkers is provided. The method comprises creating an image of one or more groups, in a cellular sample, by which each group is given a visible desgination that they belong to the same group. The images are registered to the original image of the sample to allow the images of the groups to be sequentially overlaid and analyzed In another embodiment, an image analysis system for displaying a cell and cellular components having similar patterns of expression of certain biomarkers is provided. The system comprises an imaging device adapted to capture a digital image of a cell using multiplex sequential staining to identify biomarkers within the cells; and a processing device adapted to perform the steps of generating groups based on a biomarker expression profile and to display the results.

DRAWINGS

These and other features, aspects, and advantages of the present invention will become better understood when the following detailed description is read with reference to the accompanying drawings in which like characters represent like parts throughout the drawings, wherein:

FIG. 6 is similar to FIG. 2 but in this case the cells belonging to Group 1, of the three group analysis outlined in Table 2, have been shaded in.

FIG. 7 is similar to FIG. 3 but in this case the cells belonging to Group 2, of the three group analysis outlined in Table 2, have been shaded in.

FIG. 8 is similar to FIG. 4 but in this case the cells belonging to Group 3, of the three group analysis outlined in Table 2, have been shaded in.

DETAILED DESCRIPTION

The present invention involves capturing data on the expression of biomarkers within the compartments of individual cells located within their tissue of origin, preserving this data on a cell by cell basis, analyzing this data to reveal patterns of expression, creating subsets of cells based on these patterns, visualizing the occurrence of these subsets on images of the tissues of origin and analyzing the occurrence of certain biomarkers in the subsets of cells for association to the diagnoses or prognoses of a condition or disease or to the response to treatment. In certain embodiments the data may be used to identify a biological process, a clinical diagnosis or prognosis, condition, state, or combination thereof.

The data can conveniently be initially captured by the treatment and imaging of tissue specimens. The treatment typically involves preparing slides of the tissue specimens and appropriately staining them to identify cell boundaries, cell compartment boundaries and levels of expression of selected biomarkers. The imaging typically involves digital imaging of selected fields of view from microscopic examination of the slides of the tissue specimens in a manner that the same field of view can be imaged after successive rounds of staining and the successive images can be placed in registry. The imaging also typically involves a segmentation routine that allows each pixel examined to be associated with a particular cell and a particular compartment of that cell. The data from this imaging is conveniently stored in a database such that each cell examined is associated with certain attributes reflective of the expression of the selected biomarkers within that cell. This database is then typically interrogated with numerical tools to group together those cells that have similar patterns of biomarker expression with the tools being able to create various size groups based on how similar the members of each group are to each other. One or more of these groupings can be conveniently visualized by an overlay of one or more markers or indicators on images of the tissue of origin of a given set of cells. In one embodiment an image of a selected field of view of a given slide is generated on which are marked all the cells which belong to a given group created by the application of the numerical tools. In one embodiment the pattern of biomarker expression within any given group of cells is analyzed for associations to the source of the tissue. In this embodiment tissue specimens are taken from at least two distinct groups of the same organism for instance an animal model or human subjects that differ in a biological feature under examination.

Figure 1:
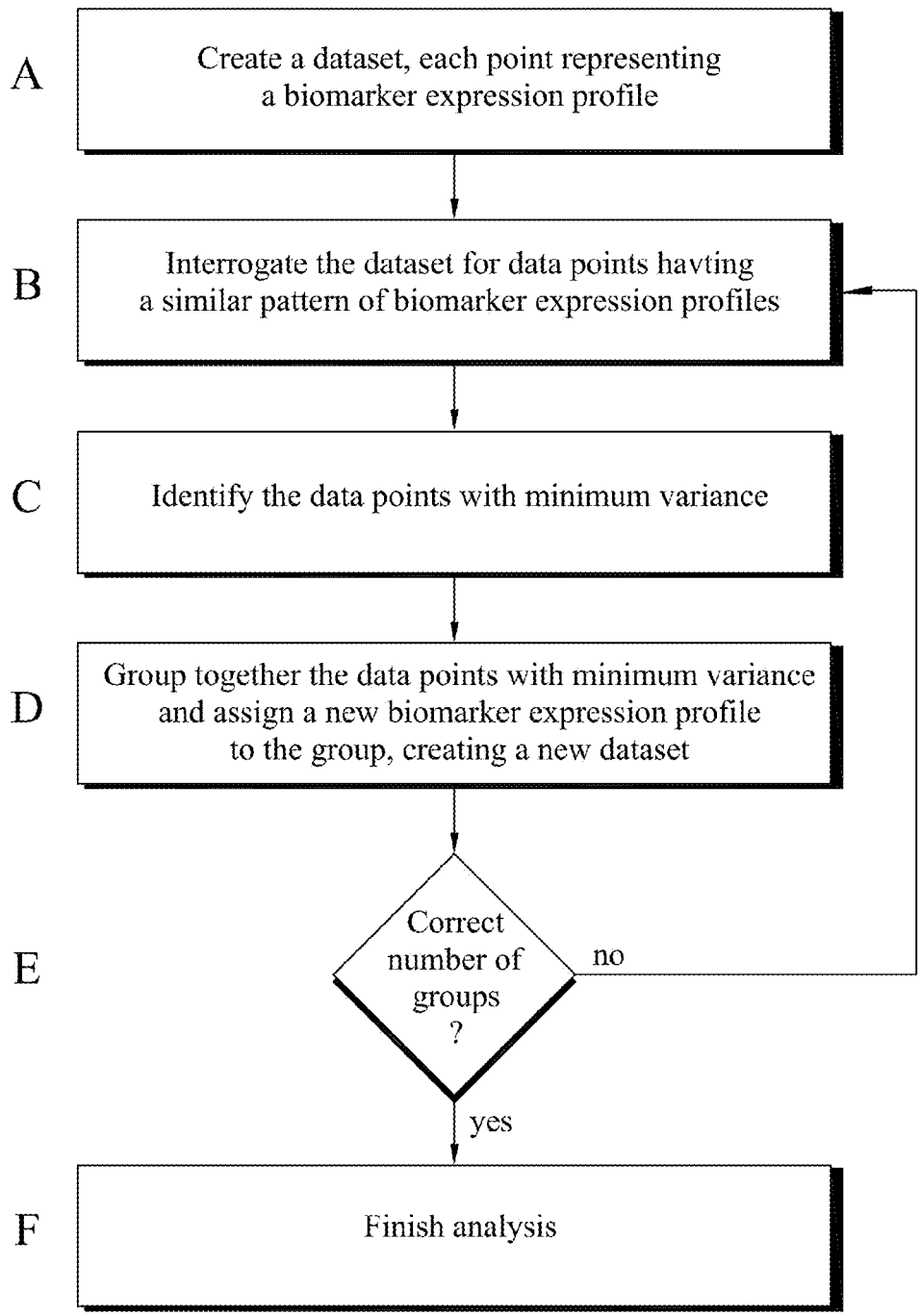
FIG. 1 is a process map illustrating the steps for analyzing the expression of biomarkers in a cell using a computer algorithm to determine similar patterns of expression.

FIG. 1 is a process map of one embodiment. The process includes creating a dataset (A) comprising a plurality of data points, each data point representing a biomarker expression profile within an individual cell. The dataset is interrogated looking for data points having similar patterns of expression (B). More specifically, each data point is compared for similarity values, using a computer algorithm wherein similarity is determined by a numerical analysis, which identifies the two or more data points with minimum variance (C). The data points having the minimum variance are grouped together and assigned a new biomarker profile, which represents a numerical averaging of the biomarker expressions of the cells as it relates to the tissue sample (D). The comparing and grouping steps are repeated on the new data set until a predetermined number of groups are generated (E).

The process describes a hierarchical approach, which allows grouping of cells that are most distinct from each other. The process may further provide for, visualizing the occurrence of these subsets on images of the tissue sample and analyzing the occurrence of certain biomarkers in the subsets of cells for association to the diagnoses or prognoses of a condition or disease or to the response to treatment.

Capturing data on the expression of biomarkers in the tissue sample may be obtained through a variety of laboratory means such as through a multiplexing staining-destaining technique. Automated image registration and analysis may also be used to quantitate the biomarker concentration levels for individual cells, or even sub-cellular compartments, such as nuclei, cytoplasm, and membrane.

The data values resulting from the multiplexing and image analysis of the tissue sample may then be subjected to further analysis. One approach is to group cells mathematically based on the expression data of biomarkers (unsupervised grouping). This mathematical approach, which may also be defined as a hierarchical or agglomerative approach, consists of sampling the data and assigning cells to the group that is most similar to their biomarker expression profile.

The data values resulting from the multiplexing and image analysis of a cell may then be subjected to further analysis. One approach is to assign groups mathematically based on the expression data of biomarkers (unsupervised grouping). This mathematical approach, which may also be defined as a hierarchical or agglomerative approach, consists of sampling the data and assigning data group to the group that is most similar to their biomarker expression profile for example to a cellular compartment within the cell such as the nucleus, cytoplasm, membrane, or other cell structure.

In one embodiment, an agglomerative approach is applied to the sub-cellular biomarker data. A sample of data may be used to develop a dendrogram, illustrative of hierarchical grouping. This analysis begins by assuming each biomarker expression is an individual group represented by a single data point. It computes the similarity values between the data points, which are an estimation of the degree of similarity between the biomarker data. In certain embodiments, the similarity value is based on the Euclidean distance in biomarker space between each data set. The two data sets that form a group with minimum variance is joined together into a group, such as a cellular component, and assigned a new biomarker value represented by a single data point. In certain embodiments, the new data point may be based on a central value for each attribute considered by the algorithm. The process is repeated until all data points are members of one large group or a predetermined number of groups. The end-user can select the number of cellular compartments, which mays also be considered as subgroups, for downstream analysis.

Alternatively the number of groups can be automatically determine for a given data set by computing the point of diminishing returns for increasing the number of identified subgroups. An advantage of the hierarchical approach is that the solution minimizes global error, thus yielding the subgroups that are most distinct from one another.

In certain embodiments, the average biomarker expression for each group is computed along with the distance in feature or value space between cellular compartment or group center. In certain embodiments the feature space is the spatial distance. This factor may be used to assign data to a particular group, such that data is assigned to the closest group within a given range of similarity values. From these assignments it is possible to assign a biomarker profile of the population that belongs to each group or cellular compartment. Expression levels are expressed relative to the mean expression of each protein for all groups.

Still in other embodiments, the numerical analysis is a rule based analysis, a classical statistical analysis, a learning algorithm or a combination thereof. Besides using Euclidean distance to estimate the degree of similarity, classical statistical analysis may also be employed as a rule based analysis of the data. In still other embodiments a neural network based learning algorithm may be employed such that data may be processed or reprocessed for grouping of the data.

In certain embodiments, the data can be initially captured by the treatment and imaging of cellular samples. The treatment typically involves preparing slides of a cellular sample, such as tissue specimens and appropriately staining them to identify cell boundaries, cell compartment boundaries and levels of expression of selected biomarkers. The imaging typically involves digital imaging of selected fields of view from microscopic examination of the slides in a manner that the same field of view can be imaged after successive rounds of staining and the successive images can be placed in registry. The imaging also typically involves a segmentation routine that allows each pixel examined to be associated with a particular cell and a particular compartment of that cell. The data from this imaging is conveniently stored in a database such that each cell examined is associated with certain attributes reflective of the expression of the selected biomarkers within that cell. This database is then typically interrogated with numerical tools to group together those cells that have similar patterns of biomarker expression with the tools being able to create various size groups based on how similar the members of each group are to each other.

One or more of these groupings can be conveniently visualized by an overlay of one or more markers or indicators on images of the tissue of origin of a given set of cells. In one embodiment an image of a selected field of view of a given slide is generated on which are marked all the cells which belong to a given group created by the application of the numerical tools. In one embodiment the pattern of biomarker expression within any given group of cells is analyzed for associations to the source of the tissue. In this embodiment tissue specimens are taken from at least two distinct groups of the same organism for instance an animal model or human subjects that differ in a biological or clinical feature under examination.

The techniques of the present invention can be applied to any tissue that is likely to vary in some manner as a result of its biological condition or history. For instance, the technique can be applied to the diagnoses of a condition by obtaining appropriate tissue specimens from subjects with and without a particular condition or disease. Thus one could take breast tissue or prostate tissue if the object were to diagnose breast or prostate cancer. Alternatively it could be applied to the prognoses of a disease or condition using appropriate historical tissue from subjects whose later clinical outcomes were known. Thus the techniques of the present invention could be applied to try to improve the prediction of survival rates in colon cancer patients from that available from the ratio of cMET expression in cytoplasm to that in membrane in which the ratio is based upon all the cells in the examined tissue. Additionally the techniques of the present invention could be applied to assess the effects of various treatments on a disease or condition. Thus one could use it to compare tumor tissue from untreated model animals to tumor tissue from model animals treated with one or more cancer drugs.

The biomarkers used in practicing the present invention may be any which are accessible to a histological examination that will give some indication of their level of occurrence or expression and are likely to vary in response to the biological condition or history of a selected tissue. The biomarkers may be DNA, RNA or protein based or a combination of them. Thus one could investigate whether there was a pattern of cells within a tissue with a given gene having a certain level of occurrence different from the average level of occurrence among all the cells in that tissue. One could similarly investigate for patterns of cells having a different level of RNA or protein expression.

The biomarkers may be conveniently selected in accordance with the biological phenomenon being examined. Thus for instance if a particular biological pathway were involved in the phenomenon under examination proteins involved in that pathway or the RNA encoding those proteins could be selected as the biomarkers. For instance, if the proliferation of neoplastic tissue were the focus the Ki67 protein marker of cell proliferation could be selected. On the other hand if the focus were on hypoxia the $Glu^1$ protein marker could be selected.

The level of expression of a biomarker of interest is conveniently assessed by staining the slides of the tissue with a probe specific to the biomarker associated with a label that can generate a signal under appropriate conditions. Two useful probes are DNA probes with sequences complimentary to the DNA or RNA of interest and antibodies or antibody surrogates such as antibody fragments with epitope specific regions that specifically bind to the biomarker of interest that may be DNA, RNA or protein. It is important that the probe be labeled in such a manner that the strength of the signal obtained from the label is representative of the amount of probe which has bound to its target.

A convenient probe from the point of view of availability and well established characterization is a monoclonal or polyclonal antibody specific for the biomarker of interest. There are commercially available antibodies specific to a wide variety of biomarkers. Mechanisms for associating many of these antibodies with labels are well established. In many cases the binding behavior of these antibodies is also well established.

A convenient label for the biomarker probes is a moiety that gives off an optical signal. A particularly convenient label is a moiety that gives off light of a defined wavelength when interrogated by light of an appropriate wavelength such as a fluorescent dye. Preferred fluorescent dyes are those that can be readily chemically conjugated to antibodies without substantially adversely affecting the ability of the antibodies to bind their targets.

A convenient approach for labeling if numerous biomarkers are to be examined is to directly label the antibodies. While there are sometimes certain advantages in using secondary or tertiary labeling like using an unlabeled primary antibody and a labeled secondary antibody against the species of the primary antibody such as signal amplification, complications may arise in finding sufficient different systems for multiple rounds of staining and bleaching.

The slides are conveniently stained with the labeled biomarker probes using well established cytology procedures. The initial staining of each slide may also involve the use of markers for one or more of the cell compartments of nucleus, cytoplasm and membrane. It is convenient to use markers such as DAPI that are not bleached when the labels attached to the biomarker probes are bleached. These procedures generally involve rendering the biomarkers in the slide tissue accessible to the labeled probes and incubating the labeled probes with the so prepared slides for an appropriate period of time. The slides can be simultaneously incubated with a number of labeled biomarker probes, each specific for a different biomarker. However, there is a practical limit to the number of labeled probes that can be simultaneously incubated with a slide because each labeled probe must generate a signal which is fairly distinguishable from the signals from the other labeled probes. A convenient approach to staining numerous biomarkers is to stain a limited number of biomarkers, take appropriate images of the stained slide and then optically or chemically bleach the labels to destroy their ability to generate signal. A further set of labeled probes specific to different biomarkers but with labeling moieties identical to those used in the prior staining step can then be used to stain the same slide. This approach can be used iteratively until images have been acquired of the same slide stained for all the biomarkers of interest. One way of implementing such an approach is set forth in U.S. Published Patent Application 2008-0118934, incorporated herein by reference.

If more than one image is taken of a given field of view it is important that the successive images, commonly collectively referred to as a stack, be kept in registry. Thus if the approach of iteratively staining and bleaching a slide is used to obtain information on numerous biomarkers it is necessary to provide a mechanism for the images of each field of view from each round to be properly aligned with the images of the same field of view from previous rounds. A convenient approach is to ensure the presence of the same feature or features in each image of a field of view. One such feature that is particularly convenient is the pattern of cell nuclei as revealed by an appropriate stain such as DAPI. One of the images can then be taken as a reference, typically the first image taken, and appropriate transformations can be applied to the other images in that stack to bring them into registry. A technique for bringing images of the same field of view into registry with each other based on their cell nuclei pattern is disclosed in U.S. Published Patent Application 2008/0032328 incorporated herein by reference.

A representative number of fields of view are typically selected for each tissue sample depending upon the nature of the sample. For instance if a slide has been has been made of a single tissue specimen numerous fields of view may be available while if the target of examination is a tissue microarray (TMA) a more limited number of fields of view may be practical.

The images of each field of view are conveniently made with a digital camera coupled with an appropriate microscope and appropriate quality control routines. For instance the microscope may be designed to capture fluorescent images and be equipped with appropriate filters as well as being controlled by software that assures proper focus and correction for auto-fluorescence. One such routine for auto-fluorescence involves taking a reference image using the filter appropriate for a given fluorescent label but with no such label active in the image and then using this reference image to subtract the auto-fluorescence at that wavelength window from an image in which the fluorescent label is active.

Each image of each field of view may then be examined for segmentation into cells and the cellular compartments of nucleus, cytoplasm and membrane, and other cellular compartments. This segmentation is typically aided by the presence of stains from markers for these three compartments. As part of the segmentation procedure each pixel of each image is associated with a particular cell and a compartment of that cell. In certain embodiments a pixel may be assigned partially to several cellular compartments according to a mathematical function. Then a value for the level of expression of each biomarker of interest is associated with each pixel from the level of signal from that pixel of the label for that biomarker. For instance if the label associated with the FOXO3a probe was Cy3, the pixels of the image of a given field of view that were stained with the labeled probe for FOXO3a would be evaluated for the fluorescent signals they exhibited in the wavelength window for Cy3. These values would then be associated with that biomarker for each of the pixels.

A database may be conveniently created in which each compartment of each cell examined is associated with a value for each biomarker evaluated which reflects the strength of the signal from the label associated with the probe for that biomarker for all the pixels or partial pixels associated with that compartment. Thus a sum is taken across all the pixels associated with a given compartment of a given cell for the signal strength associated with each biomarker evaluated.

The database may be subject to a quality control routine to eliminate cells of compromised analytic value. For instance all the cells that do not lie wholly within the field of view and any cells that do not have between 1 and 2 nuclei, a membrane and a certain area of cytoplasm may be eliminated. This typically results in the elimination of between about 25% and 30% of the data.

The remaining data in the database may now be transformed and interrogated. The data for a given biomarker across all the cells examined may not follow a distribution which readily lends itself to standard statistical treatment. Therefore it may be useful to subject it to a transformation such as a Box Cox transformation that preserves the relative rankings of the values associated with a given biomarker but places such values into an approximate Normal distribution. Then it may be helpful to standardize the values associated with each biomarker so that the values for all the biomarkers have a common base. One approach is to determine the mean value and standard distribution of all the transformed values associated with a given biomarker and then to subtract this mean value from each value in the set for that biomarker and divide the difference by the standard deviation for that transformed dataset. The database may now be interrogated for groups of cells that have similar profiles of biomarker expression.

The data on biomarker expression levels in the database may be further transformed by creating three or more intervals of value and assigning a single value to each entry that falls within a given interval. This will make the biomarker expression level a semi-continuous variable. This may be useful for reducing the computational capacity needed for the grouping algorithm, especially for particularly large datasets.

The database may be interrogated with numerical tools to group together cells with some similarity in their expression of the biomarkers being examined. In one embodiment an algorithm that can create groups at any level of similarity from treating each cell as its own group to including all the cells in a single group is used. This embodiment may use the transformed and standardized biomarker expression level data as an input and groups the cells by proximity in multi-dimensional value space. Additional cell attributes that serve as input values may include relationships between the data for different biomarkers for a given cell and relationships between the occurrences of the same biomarker in different compartments of the same cell. For instance an additional cell attribute that the grouping algorithm considers could be the ratio between the expression level of two biomarkers in that cell or it could be the ratio of expression of a given biomarker in one compartment of that cell compared to the level of expression in another compartment of that cell. In this regard the level of similarity is just a shorthand way of referring to applying the grouping algorithm to yield a given number of groups.

The numerical tools used to implement the grouping algorithm may be any of those typically used to separate data into multiple groups. These range from the straightforward application of a set of rules or criteria to the more sophisticated routines of classical statistics including probability based analysis and learning algorithms such as neural networks.

The grouping algorithm may be applied in an unsupervised fashion meaning that no constraints beyond the level of similarity are applied with regard to how it creates groups or it may be applied in a partially supervised fashion, which means one or more constraints are applied. A typical constraint could be a requirement that all the cells possessing or lacking a particular attribute be included or excluded from one or more groups for that reason. For instance, the algorithm could be applied with the constraint that all cells expressing well above the mean amount of $Glu^1$ be excluded from the groups it creates on the theory that these cells are suffering from hypoxia and therefore these cells do not provide representative information. The constraint may cause all the members of at least one group to share one or more attributes.

In an alternative approach the database may be interrogated with predefined profiles resulting in a fully supervised grouping. Thus one might extract a group of cells in which a biomarker for hypoxia, say $Glu^1$ is expressed at levels well below the mean for all the examined tissue but that the marker for cell proliferation, say Ki67, is expressed at levels well above the mean for all the examined tissue.

Another interesting approach is to combine unsupervised, partially supervised and fully supervised grouping in an iterative manner. For instance one could identify a group of cells that have a threshold level of expression of certain proteins and then create subgroups of that group using unsupervised grouping based on a panel of biomarkers that might or might not include the original criteria proteins. In another case one could create subgroups of a group created by unsupervised grouping using partially or fully supervised grouping. In another instance a group might be created by unsupervised grouping that is of particular interest and then a further application of the grouping routine could be used to identify other groups of cells that are similar to this group.

The cell attributes used to create the groups could include more than the patterns of biomarker expression. Additional attributes that could be considered include cell morphology and location in the tissue architecture such as proximity to a particular feature like a blood vessel.

The groupings created by the numerical tools or predefined profiles may be conveniently visualized by one or more overlays on images of the fields of view in which the analyzed cells appear. One approach is to take the images of one or more fields of view examined and overlay on such images symbols or colors representative of one or more of the groups such that the symbol or color representative of a given group is applied to all the cells in a given image that belong to that group. It is convenient to use an initial image or images in which cell boundaries are discernable but the signals from individual biomarkers are not displayed. In one embodiment the overlaid images are created by an electronic tool which allows the user to select the grouping iteration, i.e. the number of groups into which the cells have been classified and the number of those groups whose symbols are displayed. For instance, a user could select the grouping iteration that yielded seven groups and elect to display symbols for just two of those groups.

A numerical tool can be applied to the attribute data for all the cells belonging to a given group to determine whether there are any indications useful for diagnoses or prognoses of a disease or condition or for judging response to a treatment for a disease or condition. For instance, if samples are taken from tissue affected by a condition and tissues unaffected by the same condition all the cells belonging to a particular group can be examined to see if the cells in that group drawn digitally from tissue which are affected by the condition display any attributes which distinguish them from the cells in that group drawn from tissue unaffected by that condition.

One application could be to sample tissue affected by a neoplasm and normal tissue of the same type from the same subject or to sample tissue of the same type from subjects whose sampled tissue is cancerous and from subjects whose sampled tissue is normal. Then each group of cells created by the grouping algorithm can be examined to determine if there is any attribute or set of attributes that distinguishes cells from cancerous tissue from cells from normal tissue. In another instance historical tissue from a number of subjects with a cancerous condition whose survival rates since diagnoses are known can be examined by grouping cells and examining the attributes of the members of a group for an association with survival rates. In yet another application tissue samples could be taken from both subjects treated with a given therapy such as a drug and subjects not treated or treated with a placebo and examining all the cells in one or more groups created by the grouping algorithm for any attributes that distinguish the treated subjects from the control subjects. This approach can conveniently be applied to model animals such as mice implanted with neoplastic xenograft tissue from a human cancer.

The attributes examined may include not only the expression level and compartment location of the biomarkers evaluated but also interrelationships between these biomarkers and interrelationships between the expression levels of a given biomarker in different cellular compartments. For instance one could examine the ratio of expression levels of two biomarkers in a group of cells created by a grouping algorithm to see if the ratio could be associated with the presence of a condition or disease, the prognoses of the condition or disease or the treatment of the condition or disease with a particular therapy. One could similarly make use of the ratio of the levels of expression of a given biomarker between compartments of the same cell. In this instance it might be found that the cells from treated tissue in a given group had a different ratio of biomarker expression in the nucleus as compared to the cytoplasm for a given biomarker than the ratio for the cells for untreated tissue.

Another approach is to determine whether there is any association between the distribution of the groups and the diagnoses or prognoses of a condition or disease or the response of a condition or disease to a therapy. For instance it may be found that in tissue specimens from tissue that has gone neoplastic there are more cells in one or more of the groups than there are in healthy versions of the same tissue.

A particularly convenient statistical tool for examining the attributes of the cells in a group for indications useful for diagnoses, prognoses or treatment is "p-value" for association or probability that an observed association is the result of chance or random distribution.

EXAMPLE 1

A study was conducted on the effect of two cancer drugs and vehicle on a xenograft of human colon cancer tissue implanted in mice. Fixed, processed Xenograft tissue blocks were provided by Eli Lilly and Company (Indianapolis, Ind.) for further multiplexed analysis. A total of 39 HCT116 xenograft tumor bearing mice were treated three times a day for three days, and tumors were harvested four hours following last dose. Ten mice were treated with vehicle (DMSO), ten mice were treated with Enzastaurin at low dose (100 mpk), nine mice were treated with enzastaurin at high dose (200 mpk), Finally, 10 mice were treated with a dual PI3K/mTOR inhibitor at 30 mpk. Tumors were fixed in 10% neutral buffered formalin and processed for paraffin embedding and tissue sectioning. For the purpose of this study, tissues were sectioned from 15 animals: 5 from the vehicle treated group, 5 from the high dose Enzastaurin treated group and 5 from the dual PI3K/mTOR inhibitor treated group. The slides were baked at 65° C. for 1 hour. Paraffin was further removed from sample sections with Amresco's HistoChoice Clearing Agent for 15 minutes. The slides were then processed through a series of alcohol incubations of decreasing concentration of ethanol in water (100, 95. 70, 50%), twice at each concentration for 10 minutes, to hydrate the samples. The samples on the slides were then brought to saline conditions by incubation in PBS solution for 10 minutes. The crosslinked structures produced by formalin fixation were removed by a dual antigen retrieval method, where sample is placed in Sodium Citrate pH 6 in an pressure cooker for 25 minutes at high heat and allowed to cool to room temperature. Next, samples were transferred to a Tris/EDTA solution for another 25 minutes.

The slides prepared from the tumor tissue on each mouse were examined with a Zeiss Axiovision Z1 microscope equipped with high efficiency fluorochrome specific filter sets from Semrock for DAPI, Cy2, Cy3, and Cy5. Between 8 and 18 representative fields of interest were examined on each slide and selected for staining. Stage coordinates for each field of interest are marked using the Axiovision software and these coordinates are saved so they may be re-imaged after each staining round. A Piezzo X-Y automated stage allows the slide imaging system to repeatedly return to the same fields of interest. Fluorescence excitation is provided by a 300W Xenon lamp source (Sutter Instrument). Images are captured with a Hammamatsu ORCA-IR CCD camera using Zeiss Axiovision software with initial exposure settings determined automatically within 75% saturation of pixel intensity.

Each slide was stained in succession with ten different fluorescently labeled antibodies, each one specific for one of the ten protein biomarkers listed in Table 1. The staining methodology was similar to that disclosed in U.S. Published Patent Application 2008/00118916 incorporated herein by reference. DAPI staining was performed at the first step and was re-stained if necessary in the subsequent steps. In general each slide was stained with 2 antibodies per round, labeled with Cy2, Cy3 or Cy5 fluorescent dyes and incubated overnight at 4 C (alternatively a shorter time at room temperature is also possible). The slides were then mounted with media and coverslipped. The preselected regions of interest on each slide were imaged on the system as described above. Then each slide was removed and chemically bleached to destroy the signal from this set of fluorescent labels so that a further set of antibodies labeled with one or more of these fluorescent labels could be used. The chemical composition of the bleaching agent is described in U.S. Published Patent Application 2008/0118934, incorporated herein by reference. Then a second set of antibodies was used to stain a further two protein targets on each slide and so on until all the slides had been stained with antibodies specific to all ten protein biomarkers. Membrane regions were identified using Na-K-ATPase targeted antibodies, cytoplasm using S6 targeted antibodies and nuclei using DAPI stain. Additionally, other functional regions of interest within the tissue section were identified using Glu 1 for hypoxic regions and Ki67 for proliferating regions. One or more images were taken of each region of interest on each slide after each staining round. DAPI is not affected by the chemical bleaching agent and so the DAPI stained nuclei in each region of interest are also re-imaged in each imaging round (described in U.S. Published Patent Application 2008/0118934).

The pattern of said nuclei was used to place all the images of a given field of interest, a given stack, in registry. In particular, every image of a given field of interest captured the DAPI staining pattern showing the location of nuclei and the initial image was used as a reference to apply a rigid spatial transformation to the subsequent images so that the entire stack for that field of interest was in registry. The spatial transformation involved a global translation using a normalized correlation in a Fourier domain followed by a rotational adjustment using a normalized mutual information metric starting from the intial translation obtained from the Fourier transfrom. The registration transform was robust to intensity differences between the images in a given stack.

The auto-fluorescence, due to endogenous fluorophores in the tissue samples, was compensated for in accordance with the teachings of U.S. Patent Publication 2009/0141959 incorporated herein by reference. This involved capturing an image with an appropriate filter of each field of interest free of a given fluorescent stain and using it as a reference to remove the effects of auto-fluorescence from the image which records that fluorescent stain. As the same fluorescent dye was used multiple times the same reference image was used for correction each time a stain involving a given dye was used. In addition, another set of auto-fluorescence reference images were taken before the last three biomarkers were imaged and were used for auto-fluorescence correction for these last three biomarkers.

In the staining procedure each protein biomarker was associated with a particular fluorescent dye because the antibody used to detect that biomarker was coupled to a particular fluorescent dye. An image was then taken in the appropriate wavelength window for that fluorescent dye after the application of that antibody. Data was acquired for each compartment of each cell in each field of view representative of the level of expression of each protein biomarker for which a fluorescent stain had been applied. In particular, the intensity of the fluorescence at each pixel in each field of view was recorded for each protein biomarker.

Each pixel was associated with a particular cellular compartment of a particular cell using software algorithms. The assignment of a given pixel to a given compartment of a given cell was based on an evaluation of the morphology of the tissue observed in the field of view and the stains applied to develop the nuclei, cytoplasm and cell membranes of the cells in the field of view. Although proprietary software was used, comparable if somewhat less accurate assignments could be obtained from commercially available segmentation software.

The pixels associated with certain punitive cells were then removed from the data set as a quality control measure. In particular, pixels associated with cells that did not contain a cytoplasm and one to two nuclei were eliminated, as were those associated with cells in regions in which the image quality was poor, cells not wholly within a given field of view and cells in the top $97^{th}$ percentile in terms of cell area. Between 25% and 30% of the pixels were eliminated by this procedure.

A database was now created in which each cell remaining after the quality control procedure was associated with certain attributes including a value reflective of the auto-fluorescence corrected fluorescence intensity for each of the ten protein biomarkers evaluated in total and in each of its cellular compartments. In essence the fluorescence intensities of all the pixels associated with a given cell or a given compartment of a given cell associated with a given protein biomarker were summed. It is understood that different arithmetic expressions may also be used such as average value, median value, or other summary metric. The distribution of fluorescence intensities associated with each protein biomarker over the entire dataset was subjected to a Box Cox transformation to obtain an approximately normal distribution. In most cases this led to the application of a power function of about 0.3. Then the transformed intensity values were standardized by determining the mean intensity value and the standard deviation of intensity values and subtracting the mean value from each actual value and dividing this difference by the standard deviation. Thus each cell and each compartment of each cell was provided with a post transformation standardized value for the fluorescent intensity of each of the ten protein biomarkers. This value was taken as representative of the level of expression of that biomarker in that cell or cellular compartment.

The database was then interrogated to create groups of cells with similar patterns of protein biomarker expression. In particular, a computer algorithm was used to iteratively group cells beginning in the first iteration with placing every cell in its own group and ending in a final iteration with placing all the cells in a single group. In each intermediate iteration cells that were more similar in their patterns of protein biomarker expression were placed in the same group. The cell attributes used in this analysis were the standardized fluorescence level for each of the ten protein biomarkers and four ratios. The ratio inputs to this algorithm were for each cell the ratio of pS6 Serine 240 to S6 values, the ratio of pS6 Serine 235 to S6 values, the ratio of pAkt values in the cytoplasm to that in the membrane and the ratio of FOXO3a values in the nucleus to that in the membrane. For computational ease the grouping algorithm was applied to only 6000 representative cells, with an equal number of cells being selected from each field of view. Once biomarker profiles were created by the algorithm, these profiles were used to assign the remaining cells to appropriate groups, according to their degree of similarity in biomarker levels. For instance at the level of similarity that created three groups, three different biomarker profiles were created. The cells not part of the original 6000 cell sample were assigned to one of the three groups whose biomarker profile they most closely matched.

The expression levels of each protein biomarker, as well as each of the four ratios, was analyzed for its associations with cells belonging to the control mice, the mice treated with Enzastaurin or the mice treated with the dual PI3K/mTOR inhibitor, at each level of similarity. For biomarker similarity levels yielding a single group and three groups, only an association involving the single protein biomarker S6 was found. In the former case a higher level of expression of S6 was correlated to treatment with either of the anti-cancer drugs while in the latter case a similar association was found for just the third group of cells. For biomarker similarity levels yielding five and seven cell groups, a number of associations were found. The biomarker profiles for the three, five and seven cell groups are shown in Tables 2, 3 and 4. The associations found for the latter two biomarker similarity levels are shown in Tables 5 and 6. In profile Tables 2, 3 and 4 the occurrence of each attribute for each profile is compared to the mean value of that attribute for all the cells in the dataset. The indication "+/−" means that the value for that profile is essentially the same as the average value of that attribute for all the cells in the dataset. The indication "++" means a value of one standard deviation or more above the mean value and the indication "−−" means a value one standard deviation or more below the mean. The indications "+" and "−" mean a value between the mean and one standard deviation above or below the mean, respectively. In tables 5 and 6 the associations are reported in "p" values that indicate the probability that the observed difference between the compared groups could have occurred by chance.

Figure 2:
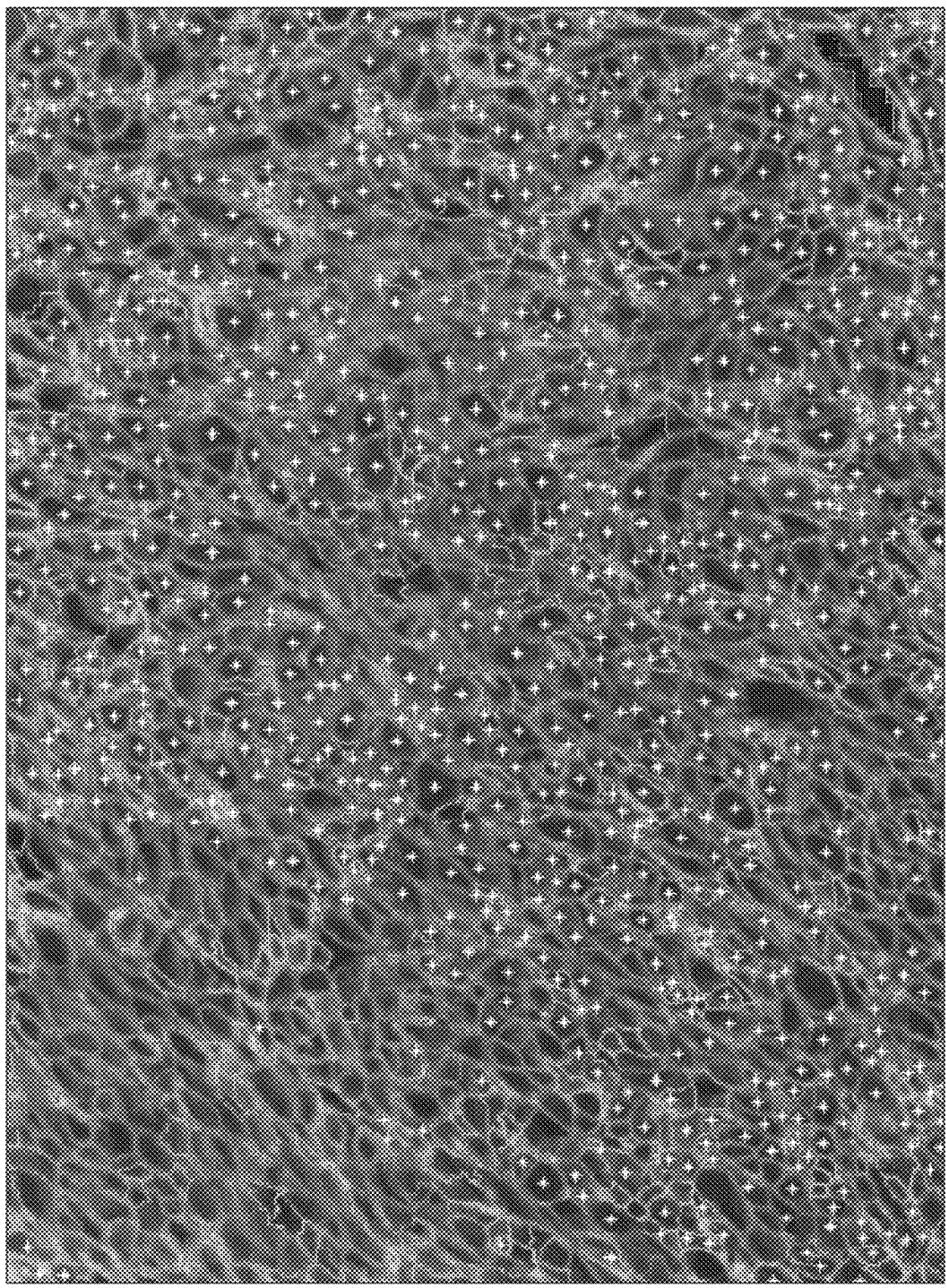
FIG. 2 is a digital image at 20× magnification of xenograft tumor tissue of human colon cancer implanted in a mouse in which those cells belonging to Group 1 of the three group analysis outlined in Table 2 have been marked with a star.
Figure 3:
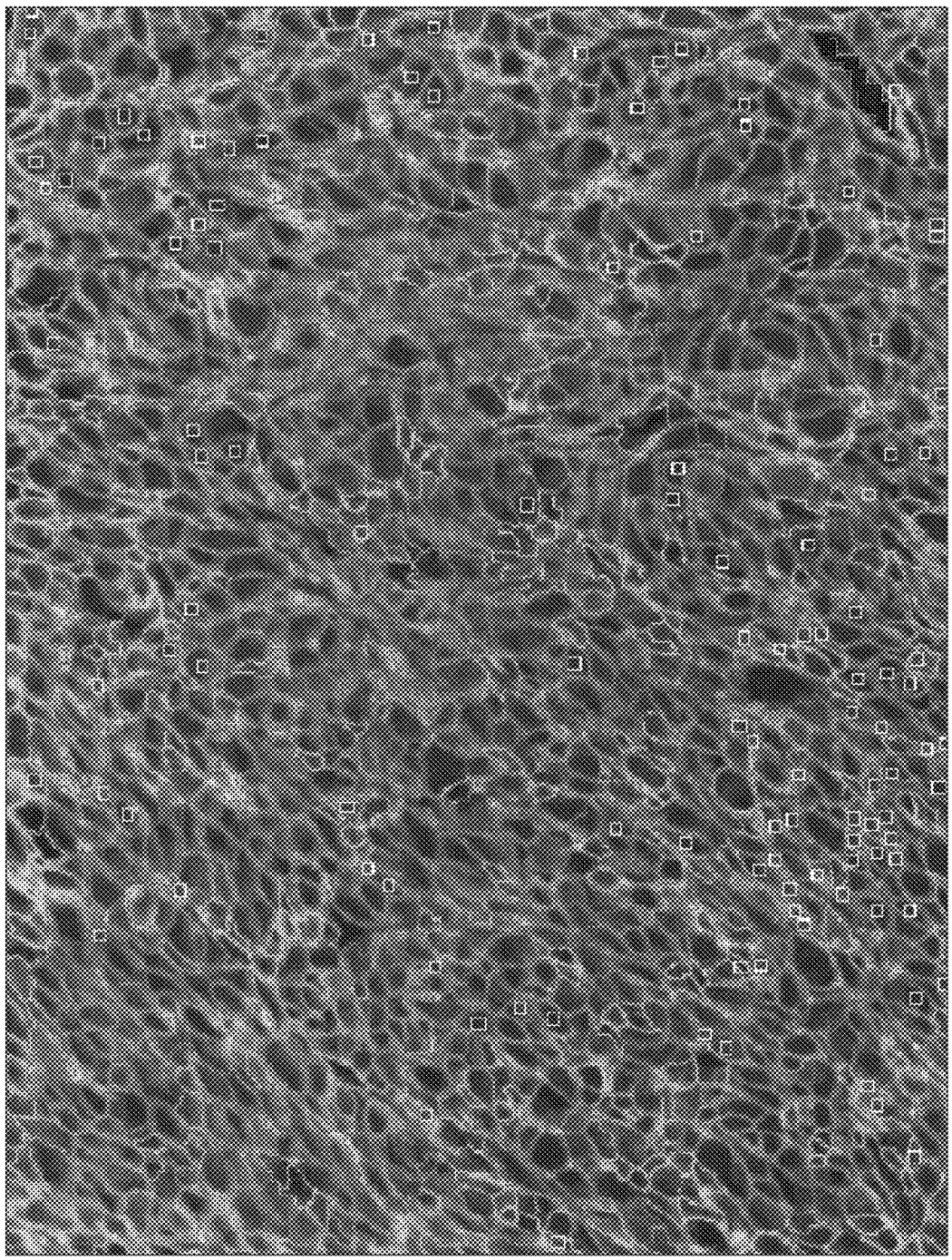
FIG. 3 is the same base image as FIG. 2 but in this case with the cells belonging to Group 2 of the three group analysis outlined in Table 2 marked with a square.
Figure 4:
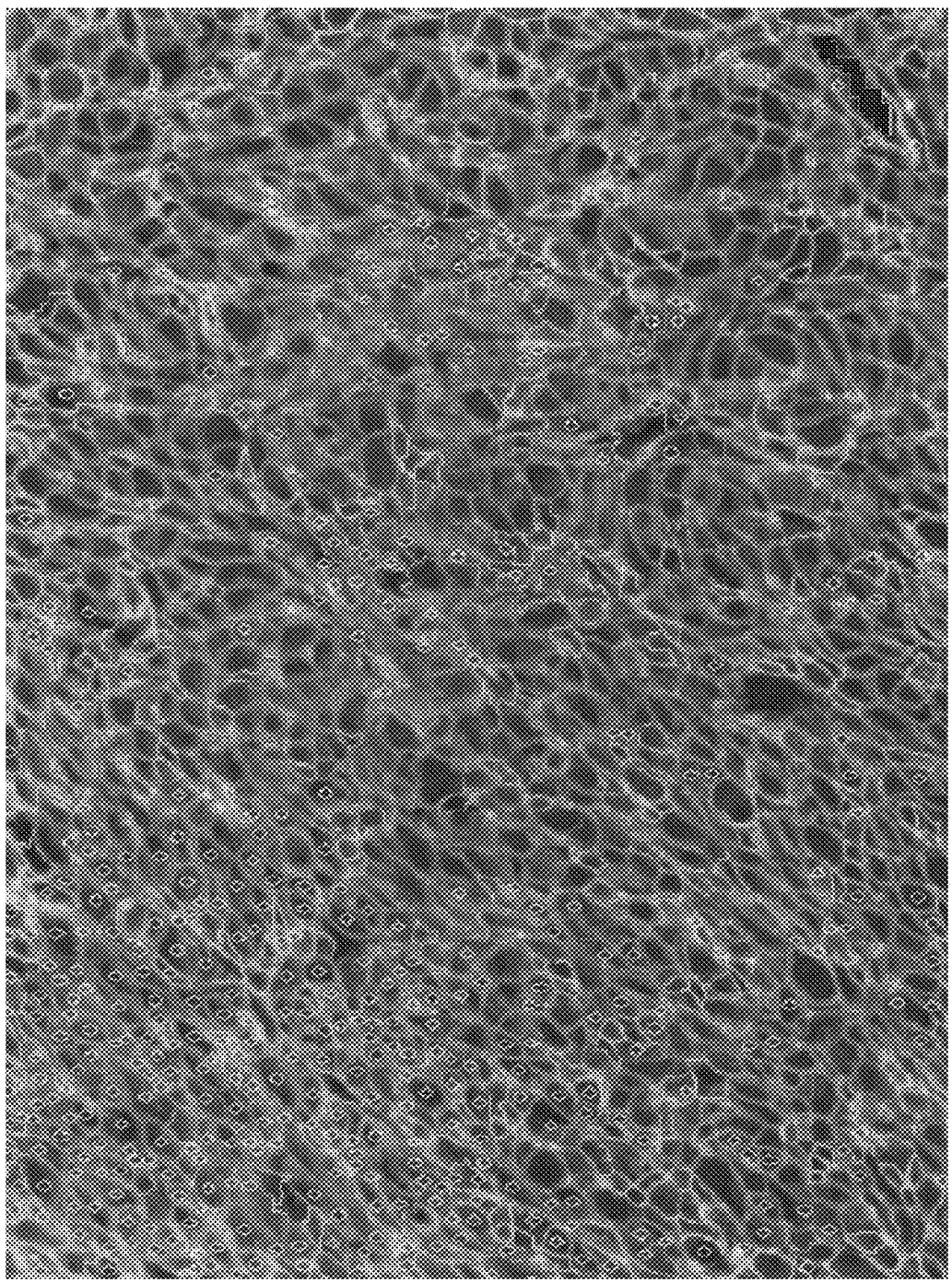
FIG. 4 is the same base image as FIG. 2 but in this case with the cells belonging to Group 3 of the three group analysis outlined in Table 2 marked with a diamond.
Figure 5:
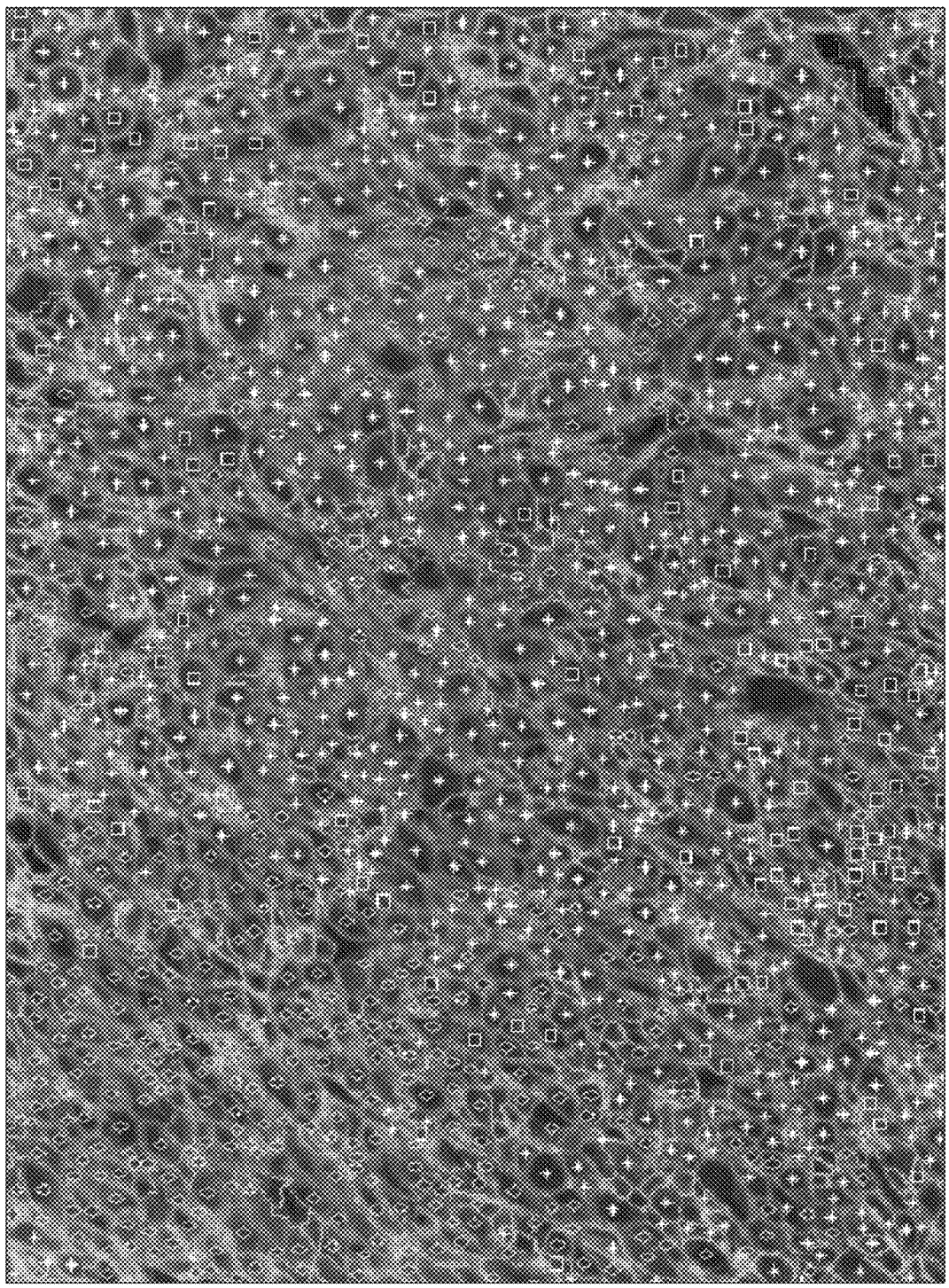
FIG. 5 is the same base image as FIG. 2 but in this case the cells have been overlaid with markers for all three groups of the three group analysis outlined in Table 2 with Group 1 marked with a star, Group 2 marked with a square and Group 3 marked with a diamond.
Figure 6:
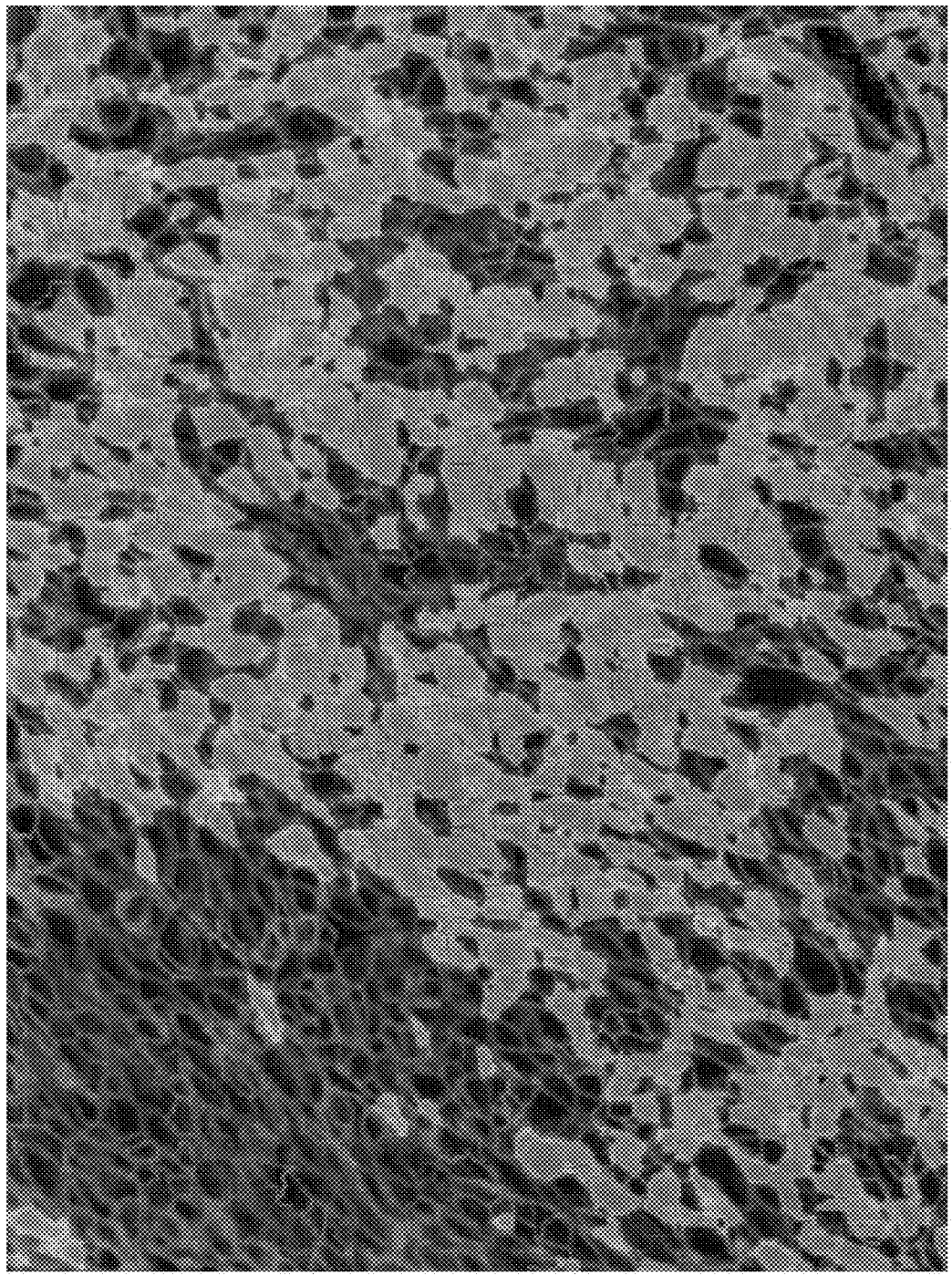
Figure 7:
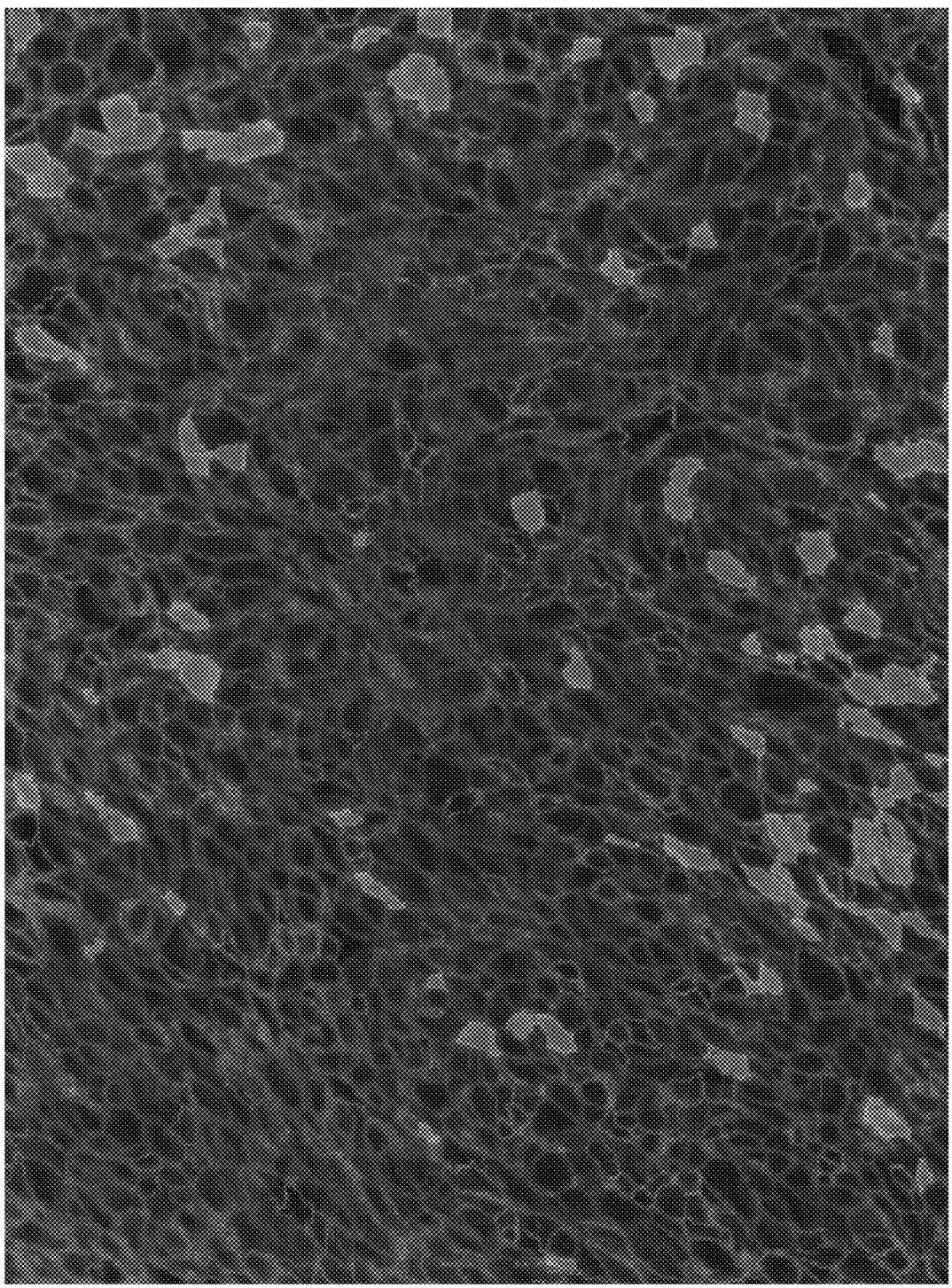
Figure 8:
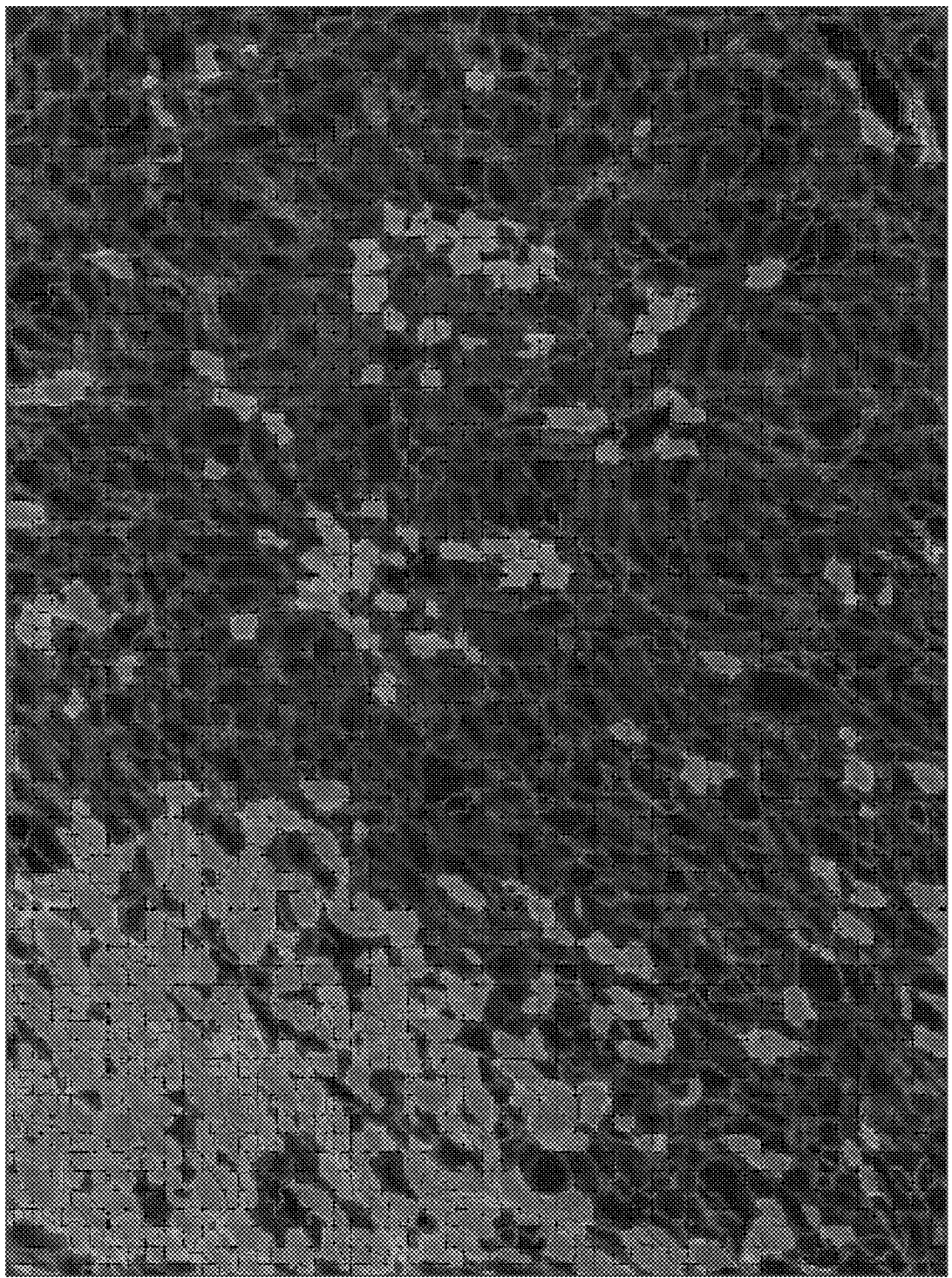

FIGS. 2-8 illustrate various ways of displaying the groups created in accordance with Table 2. FIGS. 2, 3 and 4 illustrate each of the three groups indicated by a particular symbol on an image containing cells that were examined to create the groups. FIG. 5 illustrates visualizing all three groups simultaneously using a different symbol for each. FIGS. 6, 7 and 8 illustrate an alternative technique of visualizing each of the three groups by shading in the individual cells that are members of each group.

TABLE 1

Cell Attributes Examined

| Attribute | Biomarker |
|---|---|
| Expression Level | FOXO3a |
| Expression Level | Glu1 |
| Expression Level | Ki67 |
| Expression Level | S6 |
| Expression Level | pAKt |
| Expression Level | pCREB |
| Expression Level | pCAD |
| Expression Level | pGSK3beta |
| Expression Level | pS6 Serine 235 |
| Expression Level | pS6Serine 240 |
| Ratio of Expression Levels | pS6 Serine 240/S6 |
| Ratio of Expression Levels | pS6 Serine 235/S6 |
| Ratio of Expression Levels | pAkt (cyto/mem) |
| Ratio of Expression Levels | FOXO3a (nuc/mem) |

TABLE 2

Profiles for Three Group Analysis

| Cell Attribute | Group 1 | Group 2 | Group 3 |
|---|---|---|---|
| FOXO3a Level | − | − | + |
| Glu1 Level | − | + | + |
| Ki67 Level | + | − | + |
| S6 Level | − | − | + |
| pAKt Level | − | + | + |
| pCREB Level | +/− | −− | + |
| pCAD Level | − | − | + |
| pGSK3beta Level | − | − | + |
| pS6 Serine 235 Level | − | + | − |
| pS6 Serine 240 Level | − | − | + |
| pS6 Serine 240/S6 Ratio | + | − | +/− |
| pS6 Serine 235/S6 Ratio | + | − | − |
| pAkt (cyto/mem) Ratio | + | − | +/− |
| FOXO3a (nuc/mem) Ratio | − | − | + |

TABLE 3

Profiles for Five Group Analysis

| Cell Attribute | Group 1 | Group 2 | Group 3 | Group 4 | Group 5 |
|---|---|---|---|---|---|
| FOXO3a Level | −− | − | − | + | + |
| Glu1 Level | −− | − | + | + | +/− |

TABLE 3-continued

Profiles for Five Group Analysis

| Cell Attribute | Group 1 | Group 2 | Group 3 | Group 4 | Group 5 |
|---|---|---|---|---|---|
| Ki67 Level | − | +/− | − | − | + |
| S6 Level | −− | − | − | + | + |
| pAKt Level | −− | − | − | + | + |
| pCREB Level | − | + | −− | + | + |
| pCAD Level | − | − | − | + | + |
| pGSK3beta Level | − | − | − | + | + |
| pS6 Serine 235 Level | − | +/− | ++ | + | − |
| pS6 Serine 240 Level | +/− | +/− | −− | +/− | + |
| pS6 Serine 240/S6 Ratio | + | − | −− | − | + |
| pS6 Serine 235/S6 Ratio | + | + | − | − | + |
| pAkt (cyto/mem) Ratio | + | + | − | +/− | − |
| FOXO3a (nuc/mem) Ratio | − | +/− | − | − | + |

TABLE 4

Profiles for Seven Group Analysis

| Cell Attribute | Group 1 | Group 2 | Group 3 | Group 4 | Group 5 | Group 6 | Group 7 |
|---|---|---|---|---|---|---|---|
| FOXO3a Level | −− | − | − | + | + | + | +/− |
| Glu1 Level | −− | − | − | + | + | + | − |
| Ki67 Level | − | − | − | +/− | −− | − | + |
| S6 Level | −− | − | − | + | − | + | + |
| pAKt Level | −− | − | −− | + | +/− | + | + |
| pCREB Level | − | + | −− | − | −− | + | + |
| pCAD Level | − | − | − | + | − | + | + |
| pGSK3beta Level | −− | − | − | +/− | + | ++ | + |
| PS6 Serine 235 Level | − | − | ++ | + | + | +/− | − |
| PS6 Serine 240 Level | + | − | −− | − | − | + | ++ |
| pS6 Serine 240/S6 Ratio | + | + | − | − | + | + | + |
| pS6 Serine 235/S6 Ratio | + | + | − | − | +/− | − | + |
| pAkt (cyto/mem) Ratio | + | + | + | − | +/− | + | − |
| FOXO3a (nuc/mem) Ratio | −− | +/− | − | + | − | + | + |

TABLE 5

Associations Between Treatment and Attribute for Five Group Analysis

| Cell Attribute | Group 1 | Group 2 | Group 3 | Group 4 | Group 5 |
|---|---|---|---|---|---|
| Control vs. ENZA | | | | | |
| FOXO3a Level | | | | | |
| Glu1 Level | | | | | |
| Ki67 Level | p = 0.014 (−) | | | | |
| S6 Level | | | | | p = 0.034 (+) |
| pAKt Level | | | | | |
| pCREB Level | | | | | |
| pCAD Level | | | | | |
| pGSK3beta Level | | | | | |
| pS6 Serine 235 Level | | | | | |
| pS6 Serine 240 Level | | | | | |
| pS6 Serine 240/S6 Ratio | | | | | |
| pS6 Serine 235/S6 Ratio | | | | | |
| pAkt (cyto/mem) Ratio | | | | | |
| FOXO3a (nuc/mem) Ratio | | | | | |
| Control vs. the dual PI3K/mTOR inhibitor | | | | | |
| FOXO3a Level | p = 0.034 (−) | | | | |
| Glu1 Level | | | | | |
| Ki67 Level | | | | | |
| S6 Level | | | | p = 0.032 (+) | p = 0.023 (+) |
| pAKt Level | | | | | |
| pCREB Level | | | | | |
| pCAD Level | | | | | |
| pGSK3beta Level | | | | | |
| PS6 Serine 235 Level | p = 0.033 (−) | | | | |
| PS6 Serine 240 Level | p = 0.049 (−) | | | | p = 0.021 (−) |
| pS6 Serine 240/S6 Ratio | | | | p = 0.010 (−) | |
| pS6 Serine 235/S6 Ratio | | | | | |
| pAkt (cyto/mem) Ratio | | | | p = 0.019 (−) | |
| FOXO3a (nuc/mem) Ratio | | | | | |

TABLE 6

Associations Between Treatment and Attribute for Seven Group Analysis

| Cell Attribute | Group 1 | Group 2 | Group 3 | Group 4 | Group 5 | Group 6 | Group 7 |
|---|---|---|---|---|---|---|---|
| | | | Control vs. ENZA | | | | |
| FOXO3a Level | | | | | | | |
| Glu1 Level | | | | | | | |
| Ki67 Level | p = 0.015 (−) | | | | | | |
| S6 Level | | | | p = 0.023 (+) | | | p = 0.017 (+) |
| pAKt Level | | | | | | | |
| pCREB Level | | | | p = 0.047 (+) | | | |
| pCAD Level | | | | | | | |
| pGSK3beta Level | | | | | | | |
| PS6 Serine 235 Level | | | | | | | |
| PS6 Serine 240 Level | | | | | | | |
| pS6 Serine 240/S6 Ratio | | | | | | | |
| pS6 Serine 235/S6 Ratio | | | | | | | |
| pAkt (cyto/mem) Ratio | | | | | p = 0.018 (−) | | |
| FOXO3a (nuc/mem) Ratio | | | | | | | |
| | | | Control vs. the dual PI3K/mTOR inhibitor | | | | |
| FOXO3a Level | p = 0.039 (−) | | | | | | |
| Glu1 Level | | | | | | | |
| Ki67 Level | | | | | p < 0.001 (−) | | |
| S6 Level | | | | | | | |
| pAKt Level | | | | | | | |
| pCREB Level | | | | p = 0.037 (+) | | | |
| pCAD Level | | | | | | | |
| pGSK3beta Level | | | | | | | |
| pS6 Serine 235 Level | | | | | | | |
| pS6 Serine 240 Level | p = 0.030 (−) | | | | | | p = 0.022 (−) |
| pS6 Serine 240/S6 Ratio | p = 0.033 (−) | | | | p = 0.012 (−) | p = 0.004 (−) | p = 0.013 (−) |
| pS6 Serine 235/S6 Ratio | | | | | | | |
| pAkt (cyto/mem Ratio) | | | | | p = 0.022 (−) | | |
| FOXO3a (nuc/mem) Ratio | | | | | | | |

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A process for displaying cells within a cellular sample comprising:
   a. acquiring a digital image of a cell, through microscopic examination, using multiplex sequential staining to identify multiple biomarkers within the cell comprising; iteratively staining and bleaching a slide containing the cellular sample by;
      capturing a first image;
      using a feature of the first image as a reference;
      capturing one or more successive images such having a same field of view as the first image to create an image stack;
      aligning each successive image, in the image stack with the first image using the first image as a reference;
      transforming the image stack into a digital image;
   b. transforming the digital image into a dataset comprising a plurality of data points, and placing the dataset in a registry, wherein each data point is representative of a level of expression of one of the multiple a biomarkers in the cell and where the level of expression is associated with each pixel from the level of signal from that pixel of the label for that biomarker from the sequential staining;
   c. interrogating said dataset for data points having a similar pattern of expression of said biomarkers using an algorithm wherein such similarity is determined by a numerical analysis that uses the level of expression of each of the biomarker as a semi-continuous variable;
   d. identifying two or more data points from step c, having minimum variance;
   e. grouping the data points having the minimum variance together to create a group of biomarkers whose members have a similar biomarker expression profile and assigning said group a new biomarker expression profile represented by a new data point in a new dataset, wherein said new data point is based on a central value for each attribute considered and the grouping is based on a hierarchical approach assigning the data group to the group with a similarity value closes to the biomarker expression profile;
   f. repeating steps c, d, and e until a predetermined number of groups is generated whereby the number of groups is determined using a hierarchical approach; and
   g. overlaying an image of of the resulting grouping of step f, wherein the image is registered to the digital image of the cell and creating a new image corresponding to a biomarker expression profile of said cell, wherein the groups individually represent at least one subcellular component comprising a subcellular compartment selected from a nucleus, cytoplasm or membrane.

2. The process of claim 1 wherein the image displays the groups by sequentially overlaying the groups on the digital image and by which each group is given a separate visible designation.

3. The process of claim 2 wherein the visible designation is a color, symbol, or combination thereof.

4. The process of claim 1 wherein the similarity value is based on a Euclidean distance in biomarker space between each data set.

5. The process of claim 1 wherein the similarity value is calculated using classical statistical analysis, a learning algorithm, or a combination thereof.

* * * * *